(12) United States Patent
Hamid

(10) Patent No.: US 10,363,432 B2
(45) Date of Patent: *Jul. 30, 2019

(54) SCALP-HAIR THERAPY SYSTEM

(71) Applicant: Tamim Hamid, Pleasanton, CA (US)

(72) Inventor: Tamim Hamid, Pleasanton, CA (US)

(73) Assignee: Theradome, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/669,928

(22) Filed: Aug. 5, 2017

(65) Prior Publication Data

US 2017/0333730 A1  Nov. 23, 2017

Related U.S. Application Data

(63) Continuation-in-part of application No. 14/753,000, filed on Jun. 28, 2015, now Pat. No. 9,833,633.

(51) Int. Cl.
*A61N 5/06* (2006.01)
*A61B 18/20* (2006.01)
(Continued)

(52) U.S. Cl.
CPC .......... *A61N 5/0617* (2013.01); *A61B 18/203* (2013.01); *A45D 2019/0041* (2013.01); *A61N 2005/067* (2013.01); *A61N 2005/0626* (2013.01); *A61N 2005/0647* (2013.01); *A61N 2005/0652* (2013.01); *A61N 2005/0659* (2013.01)

(58) Field of Classification Search
CPC .. A61N 5/0613; A61N 5/0616; A61N 5/0617; A61N 2005/0626; A61N 2005/0627; A61N 2005/0632; A61N 2005/0635; A61N 2005/0643; A61N 2005/0645; A61N 2005/0647; A61N 2005/0651; A61N 2005/0652; A61N 2005/0658; A61N 2005/0662; A61N 2005/067; A61B 18/20; A61B 2018/2015; A61B 2018/203
USPC ............................ 607/88–91, 100, 108, 109
See application file for complete search history.

(56) References Cited

U.S. PATENT DOCUMENTS

| 4,776,324 A * | 10/1988 | Clarren | ..................... A42B 3/00 2/171.2 |
| 7,722,656 B1 * | 5/2010 | Segal | ................... A61N 5/0617 607/88 |

(Continued)

*Primary Examiner* — Ahmed M Farah
(74) *Attorney, Agent, or Firm* — Main Law Cafe

(57) ABSTRACT

A photo-bio-stimulation device uses near infrared (NIR) laser illumination of the scalp to promote hair growth with a lightweight user wearable device. All the remaining components are mounted on the concave underside of an outer cap shell. Many VCSEL laser device chips are surface mount soldered underneath of a single large flexible printed circuit. These discrete devices direct a diffused, near uniform flood of 678-nanometer monochromatic laser light deep into the hair roots and follicles across the scalps of its users. Petal shapes along a central spine are cut deep into the side edges of the flexible printed circuit to allow it to be conformed and fixed into a hemispherical dome and attached with dozens of plastic snaps inside the outer shell. This connects inside to a rechargeable battery and power controller. A protective clear covering matching the concave underside is attached along the brims.

7 Claims, 9 Drawing Sheets

(51) Int. Cl.
  *A45D 19/00* (2006.01)
  *A61N 5/067* (2006.01)

(56) References Cited

U.S. PATENT DOCUMENTS

| | | | |
|---|---|---|---|
| 10,112,058 B2* | 10/2018 | Hamid | A61N 5/0617 |
| 2010/0106077 A1* | 4/2010 | Rabin | A61N 5/0616 |
| | | | 604/20 |
| 2011/0060266 A1* | 3/2011 | Streeter | A61N 5/0613 |
| | | | 604/20 |
| 2013/0173287 A1* | 7/2013 | Cashman | E04H 3/08 |
| | | | 705/2 |
| 2014/0296946 A1* | 10/2014 | Malek | A61N 5/0617 |
| | | | 607/89 |
| 2016/0310757 A1* | 10/2016 | Pepitone | A61N 5/0616 |
| 2017/0028216 A1* | 2/2017 | Medendorp, Jr. | A61N 5/0616 |

* cited by examiner

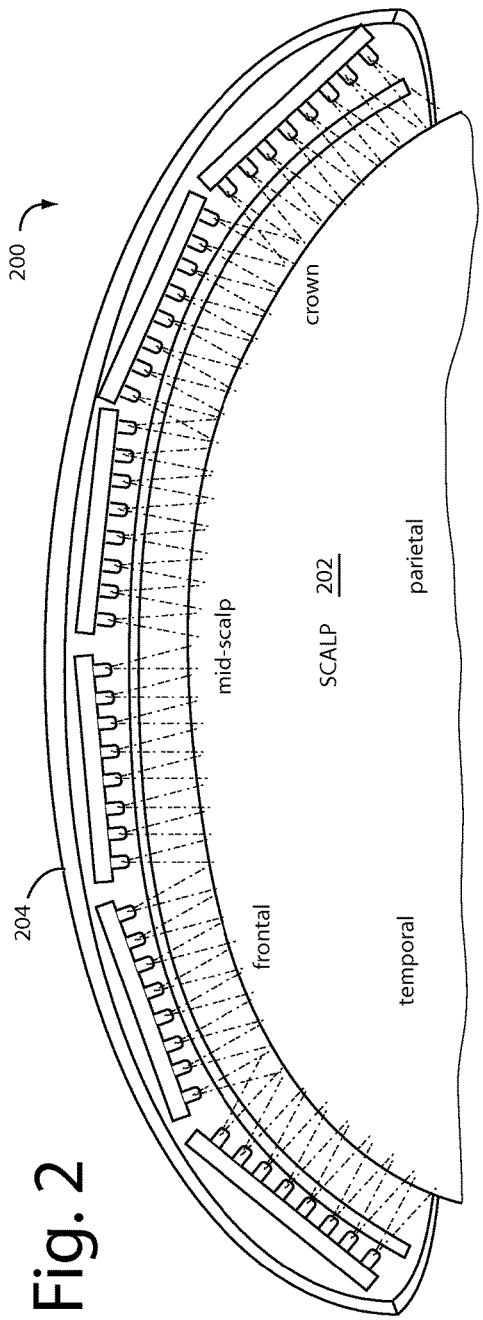
Fig. 2
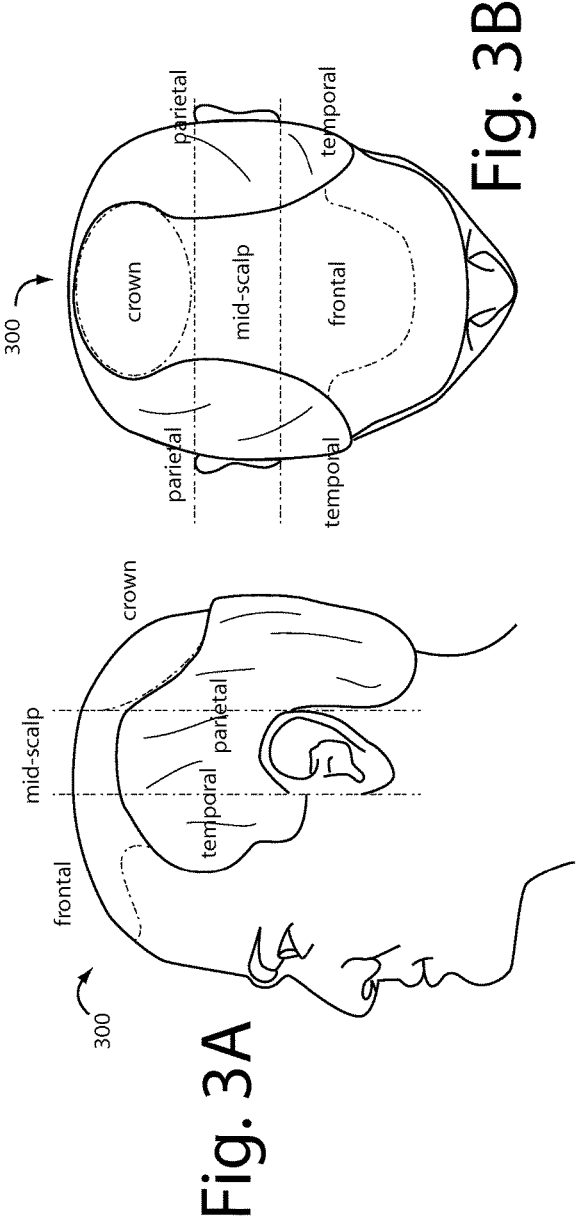
Fig. 3A
Fig. 3B

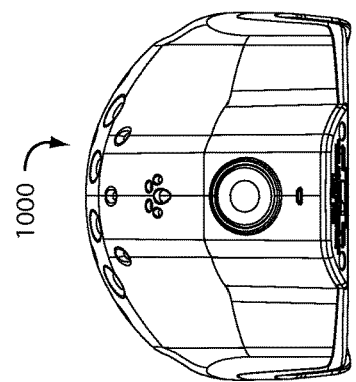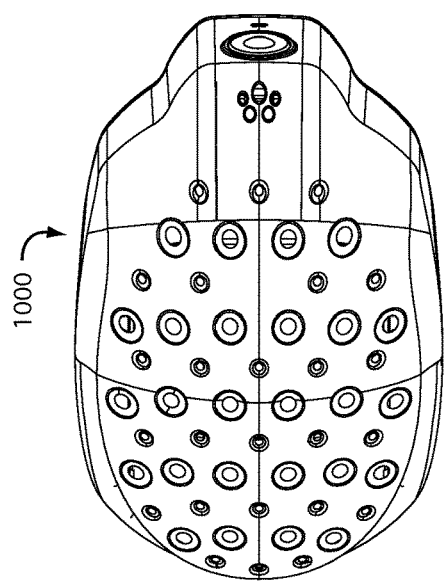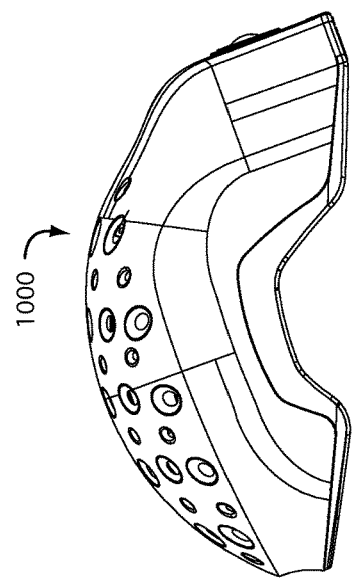
Fig. 10D
Fig. 10C
Fig. 10A
Fig. 10B

SCALP-HAIR THERAPY SYSTEM

BACKGROUND OF THE INVENTION

Field of the Invention

The present invention relates to photo-bio-stimulation devices, and more particularly to near infrared (NIR) laser illumination of the scalp to promote scalp hair growth with a helmet type wearable device.

Background

The US-FDA regulates sales of medical devices intended for the use in the diagnosis, cure, mitigation, treatment, or prevention of disease intended to affect the structure or any function of the body of humans or other animals.

Bio-stimulation lasers, also called low level laser therapy (LLLT), cold lasers, soft lasers, or laser acupuncture devices, were cleared for marketing by FDA through a Premarket Notification/510(k) process as adjunctive devices for the temporary relief of pain. These clearances were based on the presentation of clinical data to support such claims.

In January 2007, a hand-held laser therapy device was cleared by the US-FDA as a treatment for "androgenetic alopecia" (male pattern hair loss). Low Level Lasers had been previously approved by the US-FDA for the treatment for carpal tunnel syndrome, as a wound-healing aide, and as an adjunct to liposuction procedures.

Low-level laser/light therapy (LLLT), aka photo-bio-modulation and photo-bio-stimulation, has been promoted as a way to prevent hair loss and stimulate hair growth in both male and female pattern hair loss. A number of devices are marketed now for home use and are relatively simple and inexpensive. Especially when compared to conventional medical treatments and hair transplantation surgery.

SUMMARY OF THE INVENTION

Briefly, A photo-bio-stimulation device of the present invention uses near infrared (NIR) laser illumination of the scalp to promote hair growth with a lightweight user wearable device. All the remaining components are mounted on the concave underside of an outer cap shell. Many vertical cavity surface emitting laser (VCSEL) laser device chips are surface mount soldered underneath of a single large flexible printed circuit. These discrete devices direct a diffused, near uniform flood of 678-nanometer monochromatic laser light deep into the hair roots and follicles across the scalps of its users. Petal shapes along a central spine are cut deep into the side edges of the flexible printed circuit to allow it to be cupped into a hemispherical dome and attached with dozens of plastic snaps inside the outer shell. This connects inside to a rechargeable battery and power controller. A protective clear covering matching the cupped concave side is attached along the brims.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIG. 2 is a schematic diagram of the VCSEL laser device arrangement over a user's scalp, according to how they were presented in FIG. 1, and represents how the dozens of discrete VCSEL laser devices can more or less uniformly flood the entire scalp with near infrared monochromatic light; and FIGS. 3A and 3B are left side and top view diagrams of a balding man illustrating the various areas of the users' scalps referred to herein;

FIGS. 10A-10D are top, front, left, and rear views of an alternative outer shell for the flexible printed circuit with only half as many VCSEL laser devices as that of FIG. 5, in an alternative embodiment of the present invention to that shown in FIGS. 1, 2, and 6. One of the most prominent features seen here are the dozens of ventilation holes and the lack of the plate coverings necessary for simplifying the molding of the device's outer shell as shown in FIG. 6.

DETAILED DESCRIPTION OF THE INVENTION

Figure 1:
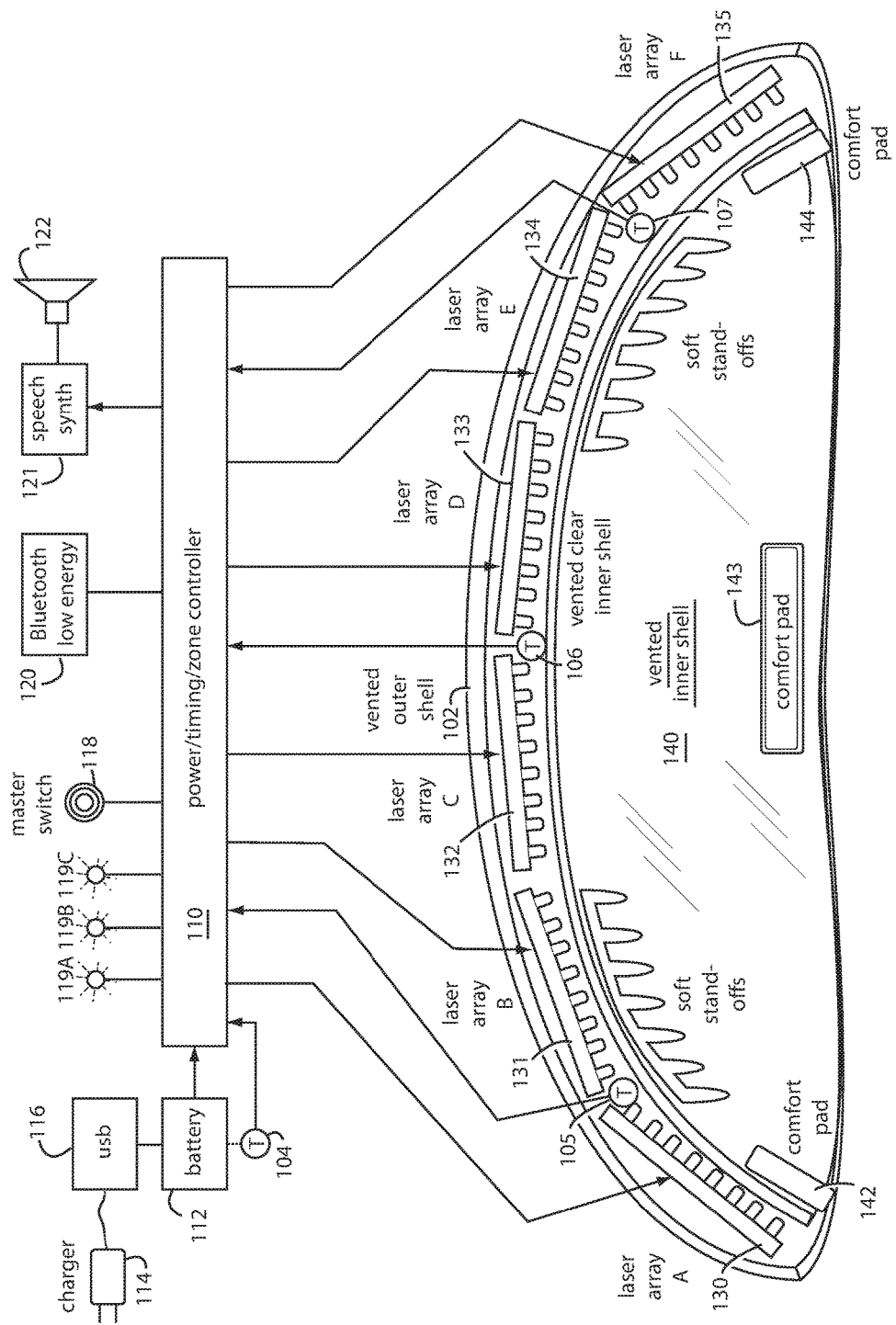
FIG. 1 is combination schematic and cutaway diagram of a light-weight, low-level laser-light scalp-hair therapy device of the present invention. The part worn by a user that faces front is shown facing left in this diagram.

FIG. 1 represents a light-weight, low-level laser-light scalp-hair therapy helmet device 100. It is shaped and sized to be worn by a user on their head for two twenty minute sessions a week. Low-level laser-light scalp-hair therapy helmet device 100 delivers a therapeutic doses of 678-nm monochromatic laser light deep into the hair roots and follicles. The less hair there is, the more low-level laser-light will be able to reach into the top surface layers of the scalp. Human skin tissues are translucent to light at these wavelengths.

Single wavelength monochromatic light from vertical cavity surface emitting laser (VCSEL) devices is preferred over light emitting diodes (LED's).

Human tissues are such that light at wavelengths in the near-infrared (NIR) region penetrate deeply and with minimal absorption through high scattering. A first NIR "optical tissue window" is conventionally known to admit wavelengths in the range of 650-950 nm. Longer NIR wavelengths suffer from water absorption peaks, and a dearth of NIR-CCD detectors has hindered scientific observations. A second NIR spectral window exists from 1100 to 1350 nm. A new third NIR optical window was only recently identified in the range of 1600-1870 nm. A possible fourth optical window seems to be centered at 2200 nm.

Low-level laser-light scalp-hair therapy helmet device 100 includes an outer shell 102 that supports all the other components in one assembly. Such outer shell 102 is vented to allow heated air to escape and a cooling flow of air from beneath to circulate through. Excessive heat buildup is to be avoided, it can cause discomfort to the user, it will reduce the conversion efficiencies of the laser devices, and components like batteries can be damaged. The loss of conversion efficiencies of the laser devices not only causes battery power to be wasted, it causes less of the therapeutic laser light to be delivered into the scalp.

A number of sensors 104-107 provide a mixture of temperature and/or proximity detection. They are used to sense battery temperature of rechargeable battery 112 and the temperature of vented inner shell 140. The object of the battery temperature measurement is to allow a controller 110 to shut off the battery load if it's overheating. For example, the battery is rated for 2200-milliamp hour @ 3.7-VDC. The object of the vented inner shell temperature measurement is to allow the controller 110 to shut off the laser arrays 130-135 and prevent more than a two-degree Fahrenheit (2-F°) temperature rise of the user scalp over ambient. At least one sensor 104-107 detects the proximity of user scalp 202 (FIG. 2), and controller 110 is programmed to shutdown power and operation if the user is not actually wearing the helmet device 100.

A popular-type USB charger 114 plugs into a micro-USB socket 116 to charge battery 112. Alternatively, a charge can be received from a conventional USB connection to a laptop computer. A master switch 118 controls basic on/off functions and can be manipulated to produce alternative operational modes in power/timing/zone controller 110. It is fitted inside with red-green-yellow LED lights 119A-119C to visually provide operational status feedback to local users.

A Bluetooth low energy (BLE) wireless transceiver 120 supports Internet communication and reporting of the operational status, therapy logs, and use profiles collected, processed, stored, and provided by controller 110 to a centralized server. WiFi and other types of wireless transceivers can also be used for communication with the Internet and specialized servers in virtual private networks (VPNs). In future, a better wireless solution than BLE may present itself, but for right now BLE seems a good choice.

A speech synthesizer 121 and a loudspeaker 122 are included to speak operational instructions and status to the user. Several different languages can be selected to be spoken. The vocabulary and phrases used in such speech are very simple.

Several laser arrays A-F 130-135 are mounted inside the outer shell 102 in an overhead arch. These laser arrays A-F 130-135 are generally about an inch or two square and arranged in tiles for 100% laser light coverage of the user's entire scalp. The users' scalps may be divided into zones, e.g., the frontal scalp, parietal scalp, and temporal scalp (FIGS. 3A-3B).

However, in current embodiments we've found it best to treat all areas of the scalp together at the same time and not divide treatments into zones.

The power/timing/zone controller 110 allows the laser arrays A-F 130-135 to be switched on/off to limit laser-light therapy to just one or more of the scalp zones. The power/timing/zone controller 110 also limits exposure times and can shut off power early if the user's scalp is not detected at all with a proximity sensor. A full therapy session is twenty minutes in duration.

In one example shown here, a total of eighty vertical-cavity surface-emitting laser (VCSEL) devices capable of delivering 3-6 joules of light energy per square centimeter of scalp are arranged on the several laser arrays A-F 130-135. The precise number of VCSEL devices employed is less important that the coverage and exposures actually realized in use. Lenses and diffusers could be used to economize on the number of VCSEL devices, and/or make what there are more effective.

The target range of therapeutic amounts of energy delivered to the scalp appear to be in the range of 3-6 joules/cm$^2$ over a twenty minute session. About 4-6 joules/cm$^2$ of energy is considered to be optimum. The total in joules is equal to the number of watts per diode, times the number of VCSELs, multiplied by the time in seconds. The energy density, (J/cm$^2$)=watts per VCSEL multiplied by time in seconds divided by the coverage area (cm$^2$). Treatment time (secs)=energy density (J/cm$^2$)/output power density (W/cm$^2$).

Newer future products are contemplated to employ only forty VCSEL's total.

The operational distances, and thus the ambient light levels delivered by the many VCSEL's to the users' scalps must be consistent, uniform, and controlled. One centimeter spacers are used to limit the VCSEL-to-scalp separation distance. The area spacing between VCSEL's is empirically determined to provide balanced light uniformity. The power/timing/zone controller 110 is used for dynamic on/off control. It could modulate the electrical power it switches to the VCSEL's to control light intensities on the users' scalps.

A vented clear inner shell 140 is mounted with spacers to the outer shell 102 and protects the several laser arrays A-F 130-135 from being rubbed, scraped, or torn by the users. A number of sponge rubber stick-on comfort pads 142-144 are provided loose for the users to place them inside the inner shell 140 at points they like best.

Controller 110 maintains the operational status and therapy logs for helmet device 100, e.g., with a microcontroller and non-volatile flash memory. Controller 110 is disposed on a flexible printed circuit with the plurality of individually controllable laser arrays and connected to control each according to predefined therapeutic profiles and sessions, and that maintains an operational status and log with a microcontroller or microcomputer.

Controller 110 has logic to automatically turn on/off specific frontal-midscalp-crown-temporal-parietal zones (FIG. 2) of the scalp corresponding to laser arrays 130-135. The distance from the laser devices to scalp will principally determine the scalp area coverage and any hot spots. Several one centimeter spacers are therefore included to maintain a uniform separation distance off the user's scalp.

FIG. 2 represents a VCSEL laser device arrangement 200 over a user's scalp 202 with a wearable device 204, according to how they were presented in FIG. 1. FIG. 2 further represents how dozens of discrete VCSEL laser devices can more or less uniformly flood the entire scalp 202 with near infrared monochromatic light Referring now to FIGS. 3A and 3B, the frontal scalp area of a typical user 300 is aft of the front hairline and back to a line drawn up in front of the ears and laterally as wide as the outside of the eyelids. The crown scalp is an oval area that starts just aft of a line drawn up in back of the ears and immediately above the upper margins of the occipital hair. The crown area is often the first and more visible area of hair thinning. The mid scalp area is the relatively flat part directly over the top and from ear to ear. Temple areas are above and forward of the ears on each side. The parietal area is between temple and occipital scalp. The occipital area lies behind the parietal area, superior to it lies the crown area and it extend below into the nape of the neck.

Figure 4:
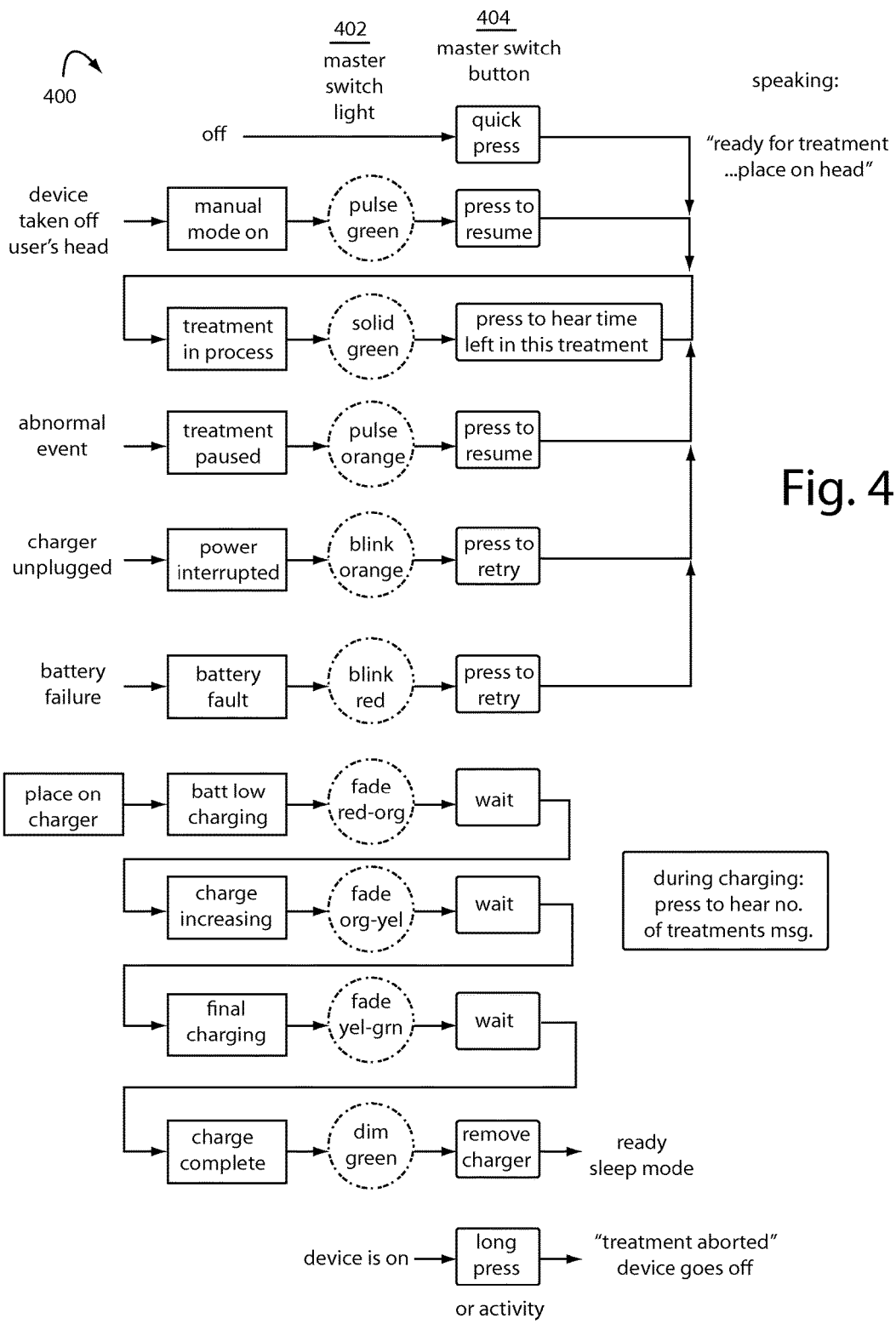
FIG. 4 is a flowchart diagram representing how the digital logic devices inside the power/timing/zone controller of FIG. 1 are ordered to function in response to the master-switch, and how the colors and durations of red-green-yellow lights mounted inside the master-switch can provide a simple but easy-to-understand operational status.

FIG. 4 uses a flowchart diagram to represent how the digital logic devices inside power/timing/zone controller 110 (FIG. 1) are ordered to function in response to the master-switch, and how the colors and durations of red-green-yellow lights 119 mounted inside the master-switch 118 can provide a simple but easy-to-understand operational status.

Figure 5:
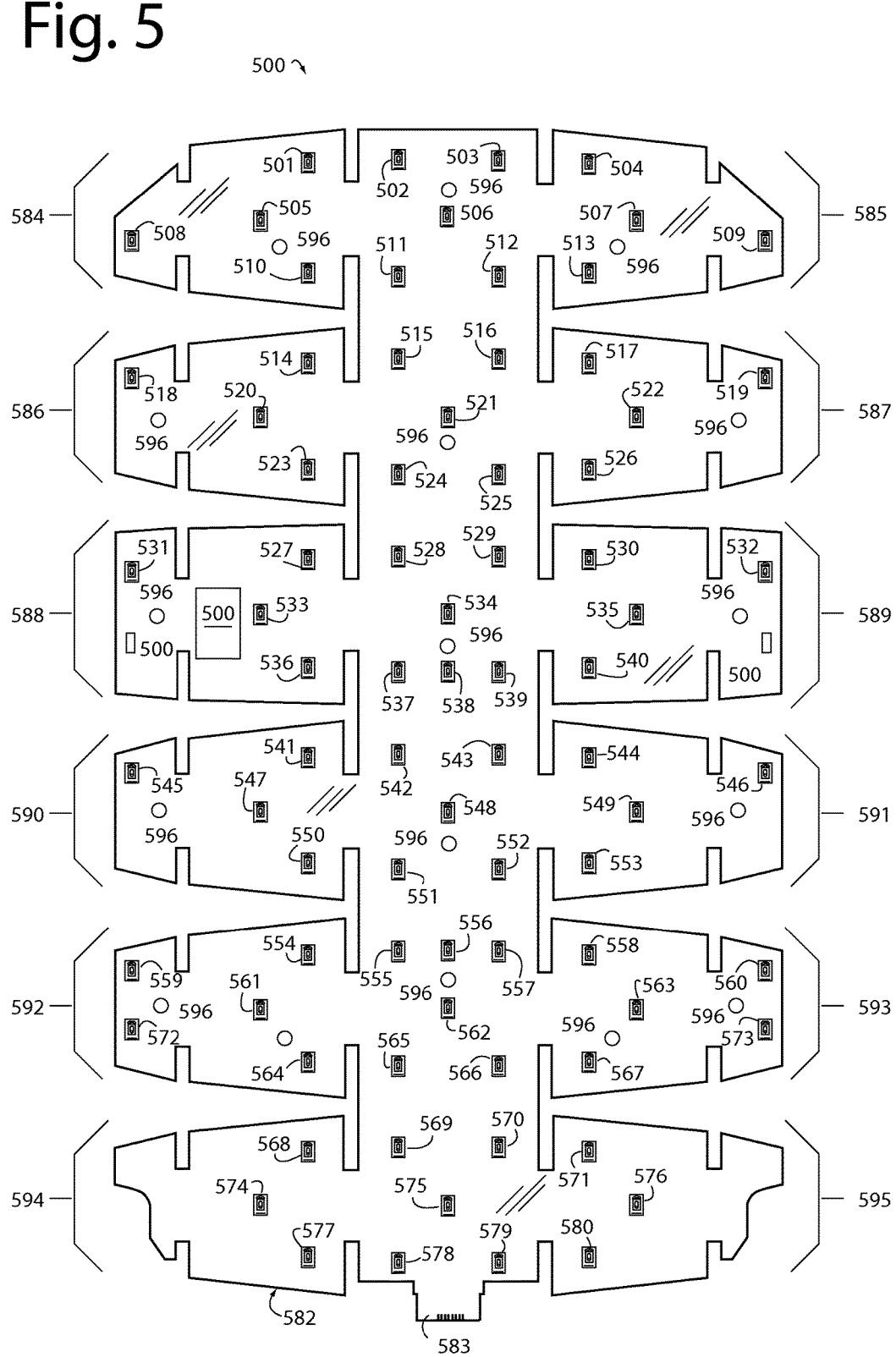
FIG. 5 is a plan view diagram of the underside of the large flexible printed circuit that supports and drives the many VCSEL laser devices. The placement patterns are designed to help distribute the therapeutic light evenly and efficiency across the entire scalps of its users.

FIG. 5 represents the underside of a large flexible printed circuit assembly 500 that supports and drives (here) as many as eighty surface mount soldered VCSEL laser device chips 501-580. The placement patterns are designed to help distribute the therapeutic light evenly and efficiency across the entire scalps of its users. All these VCSEL laser device chips 501-580 are attached to a single flexible printed circuit 582. An edge connector 583 provides the electrical connections necessary for the VCSEL laser device chips 501-580 to be powered in a number of scalp zones.

In this example, twelve "petals" 584-595 along a central spine are trimmed out deep into the side edges of flexible printed circuit 582 to allow it to be cupped roughly into a hemispherical dome and attached with dozens of plastic snaps inside the outer shell using holes 596. A typical flexible printed circuit 582 is about 7.0" wide and 13" long.

The flexible printed circuit assembly 500 connects inside laser-light scalp-hair therapy helmet device 100 to the rechargeable battery 112 and power/timing/zone controller 110 (FIG. 1). A protective clear covering 140 (FIG. 1) matching the cupped concave side is attached along the edges and brims to provide a minimum scalp spacing and to prevent abrasion to the VCSEL laser device chips 501-580 during use.

A proximity circuit 597 detects when the user has removed the laser-light scalp-hair therapy helmet device 100 from their heads, or put it back on.

Figure 6:
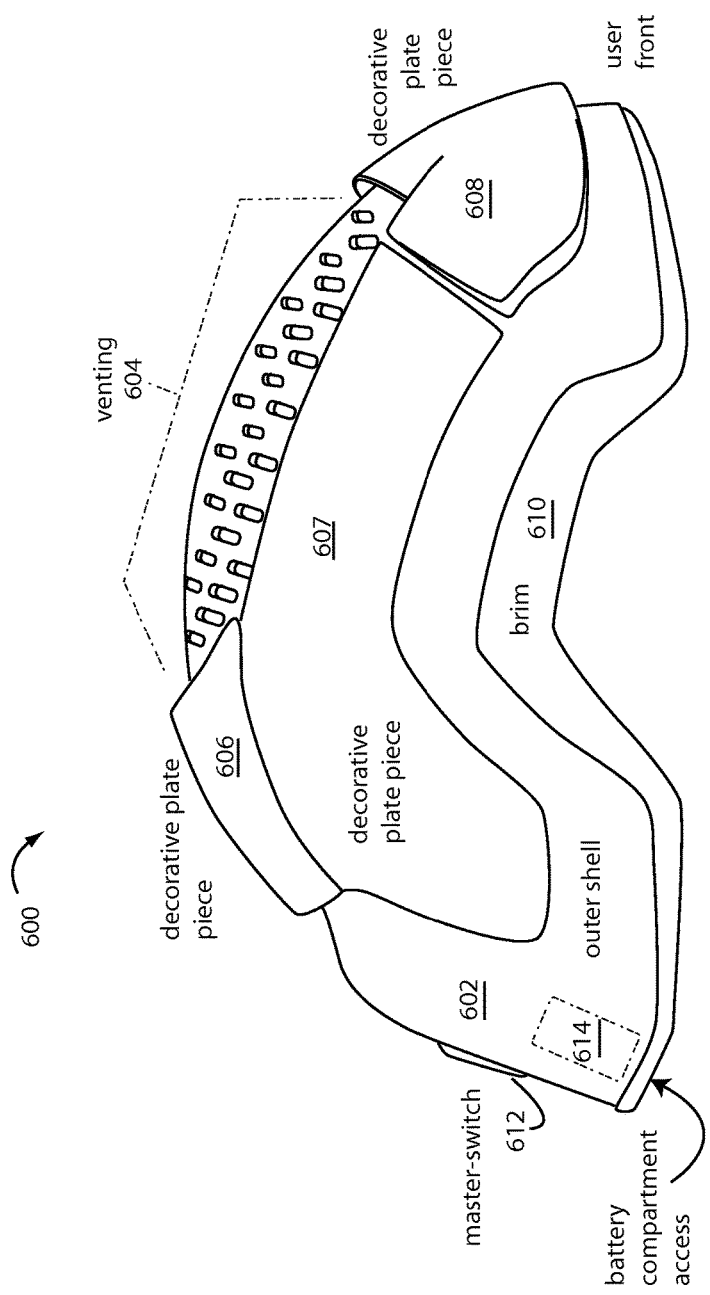
FIG. 6 is a right side view diagram of a low-level laser-light scalp-hair therapy device of the present invention for wearing on the head by a user during twenty minute treatments.

FIG. 6 represents one way that the a light-weight, low-level laser-light scalp-hair therapy helmet device 100 can be designed for commercial appeal. Here, a light-weight, low-level laser-light scalp-hair therapy device 600 gives the general appearance of a quality bicycle helmet. It is executed in attractive white and light blue colored injection-molded plastics. Injection molding techniques lend themselves to efficient, low-cost, mass production. The whole assembly is about 11" by 8" by 6".

An outer shell 602 in white plastic has an area 604 of venting to help keep the users' heads and helmet device 100 as cool as possible. Even a little excess heat trapped inside can cause user discomfort, fatigue, and degraded performance of the VCSEL chip devices. What appear to be simple decorative plate pieces 606-608 executed in a matching white injection molded plastic, are in fact studded underneath with bosses that protrude through reliefs in the outer shell 602 to provide dozens of standoff posts at the best angles to which flexible printed circuit assembly 500 (FIG. 5) can be attached during manufacturing. These same studded bosses would be very expensive and difficult to include in the production molds that make outer shell 602.

The simple decorative plate pieces 606-608 each have 2-3 Philips sheet metal fasteners that fix them solidly to outer shell 602.

A brim 610 in light blue injection molded plastic has inner shell 140 (FIG. 1) inserted into its field. The inner shell 140 is executed in clear injected molded plastic and includes dozens of vents. Brim 610 attaches to outer shell 602 with four Philips sheet metal fasteners. A master-switch 612 and a battery 614 are mounted in the rear.

Figure 7:
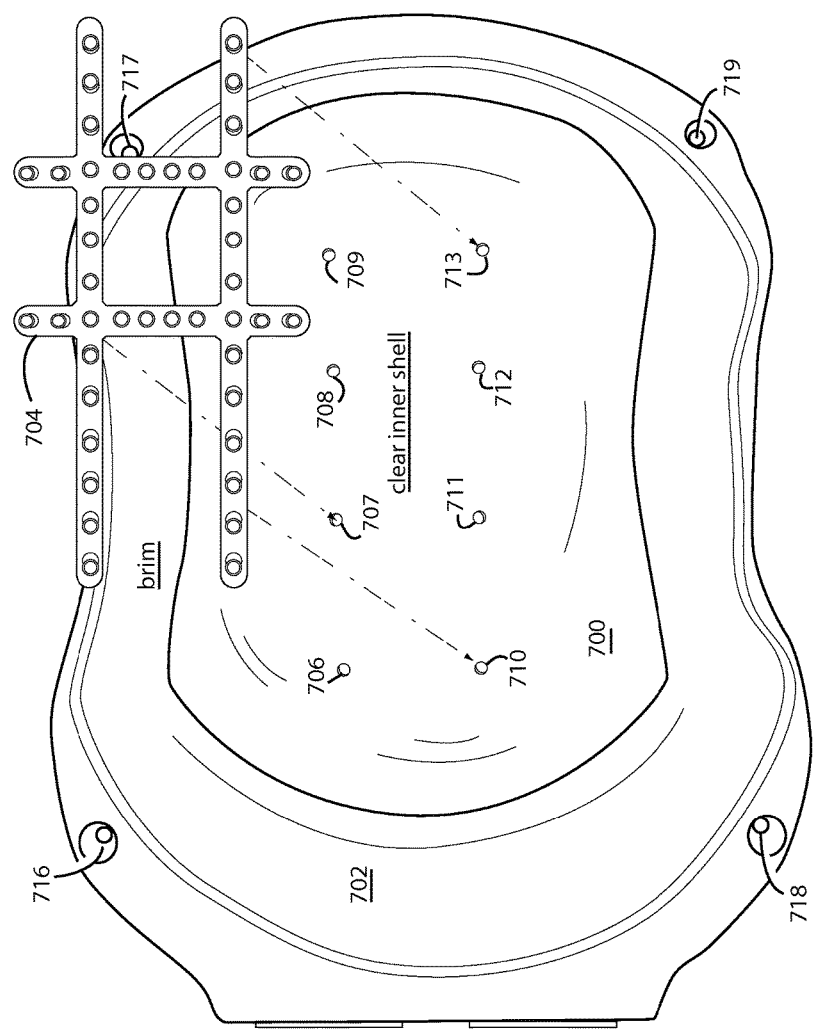
FIG. 7 is an assembly view diagram of the bottom of the clear plastic inner shell and its surrounding opaque brim. The rear of the device is to the left in the illustration. A rubber peg H-bridge is assembled inside the concave interior of the clear inner shell and retained by eight integrated rubber snap-in anchors (better seen in FIG. 8). An opaque peripheral brim joins the inner shell to the outer shell with four sheet metal screws.

FIG. 7 represents how a clear plastic inner shell 700 (140, in FIG. 1) can be molded to be joined to a surrounding brim 702 (610, in FIG. 6). A rubber peg H-bridge 704 is molded of very soft and translucent rubber, and then assembled inside the concave interior of the clear inner shell and retained by eight rubber snap-in anchors (better seen in FIG. 8) that respectively plug into eight retaining holes 706-713. The peripheral brim 702 is typically opaque, maybe light blue for aesthetic appeal, and joins the inner shell 700 to the outer shell (102, FIG. 1) with four sheet metal fastener screws using screw holes 716-719.

Figure 8:
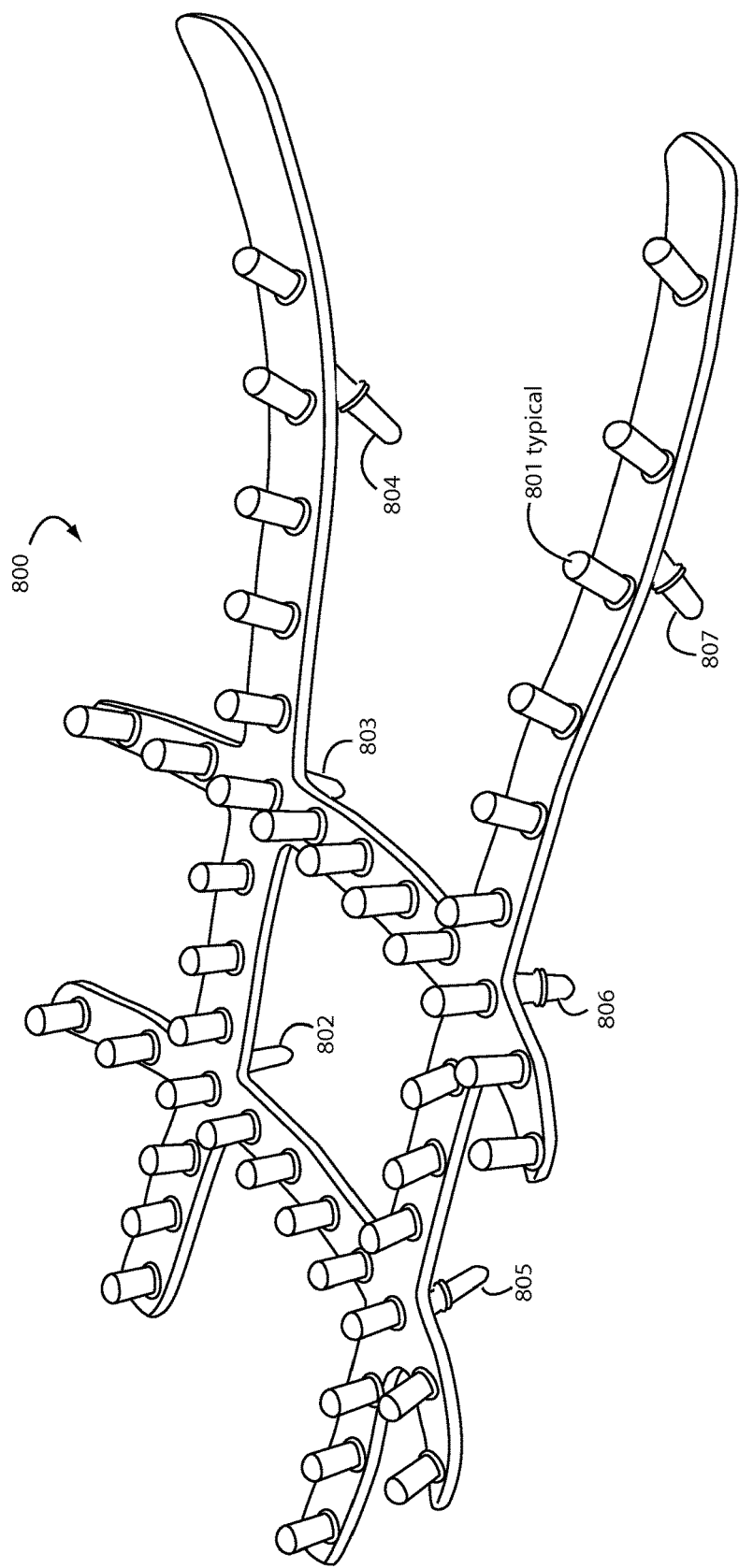
FIG. 8 is a perspective view diagram of the rubber peg H-bridge showing how the individual pegs that rest on a user's scalp are molded with various outward tilts that compensate for the bias caused to them when the whole is fitted within the concave interior of the inner shell.

FIG. 8 represents a rubber peg H-bridge 800 and the dozens of individual rubber pegs 801 that normally point straight down and rest on a user's scalp. Each Rubber peg 801 serves three purposes. First, they keep the separation distance between each laser and the scalp consistent. Second, they make for a soft mechanism for resting the helmet on the scalp. And third, they are a method of exposing the scalp by parting hairs as the helmet is placed on the head.

Rubber pegs 801 are molded with a variety of outward tilts that compensate for the bias caused to them when the whole H-bridge 800 is fixed within the concave interior of the inner shell. The objective is shown to some extent in FIG. 1 in which the soft standoff pegs all become parallel and point straight down to align with gravity. A number of pull-through snap in anchors 802-807 are used to retain the H-bridge 800 instead of adhesives.

Figure 9:
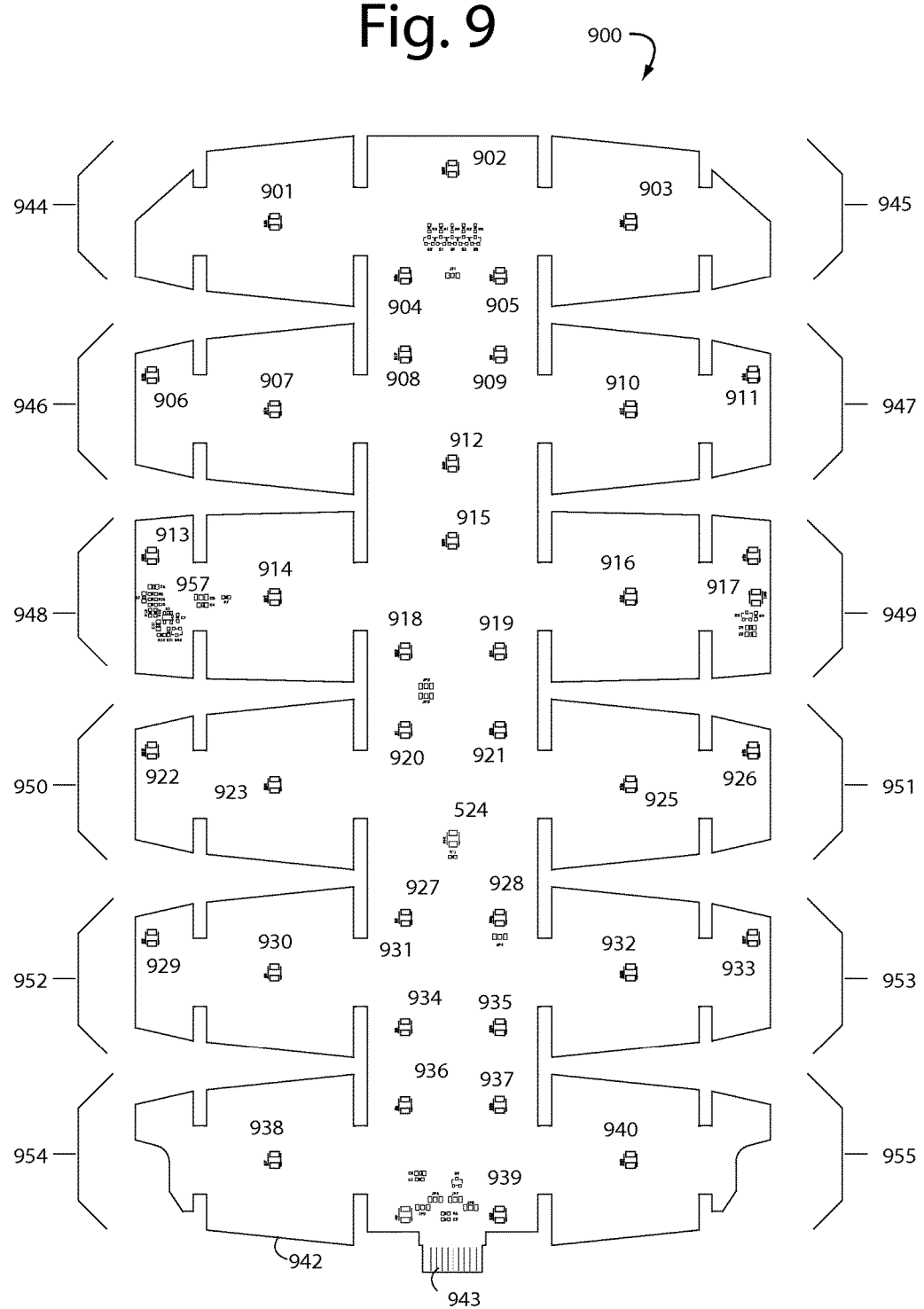
FIG. 9 is a plan view diagram of the underside of a flexible printed circuit with only half as many VCSEL laser devices as that of FIG. 5, in an alternative embodiment of the present invention.

FIG. 9 represents a flexible printed circuit embodiment of the present invention with only half as many VCSEL laser devices as that of FIG. 5, in an alternative embodiment of the present invention referred to herein by the general reference numeral 900. Flexible printed circuit assembly 900 that supports and drives only half as many as surface mount soldered VCSEL laser device chips 901-940. One placement pattern designed to help distribute the therapeutic light evenly and efficiently is illustrated in FIG. 9. The VCSEL laser device chips 901-940 are typically attached to a single flexible printed circuit 942 using solder surface mount technology. An edge connector 943 provides the electrical connections necessary for the VCSEL laser device chips 901-940 to be powered as groups in a number of scalp zones.

Here, twelve "petals" 944-955 along a central spine are trimmed out deep into the side edges of flexible printed circuit 942 to allow it to be cupped roughly into a hemispherical dome and attached inside the outer shell. A typical flexible printed circuit 942 is about 7.0" wide and 13" long.

The flexible printed circuit assembly 900 connects inside laser-light scalp-hair therapy device to a rechargeable battery and power/timing/zone controller (e.g., FIG. 1). A protective clear covering matching the cupped concave side is attached along the edges and brims to provide a minimum scalp spacing and to prevent abrasion to the VCSEL laser device chips 901-940 during use.

A proximity circuit 957 detects when the user has removed the laser-light scalp-hair therapy device from their heads, or put it back on. If taken off, power to the lasers is turned off.

By way of comparison of using eighty VCSEL laser devices versus forty, TABLE I contrasts some of the more important parameters. In practice, a hundred VCSEL laser devices may be wasteful and too many, while only one would be insufficient in its coverage and inadequate. Some number in between would strike a balance between costs and results.

TABLE I

| Item | 80-VCSEL | 40-VCSEL | Comments |
|---|---|---|---|
| Laser Class | 3R | 3R | Same |
| Number of Laser Diodes | 80 | 40 | 40 in same locations in 80-VCSEL |
| Wavelength | 678 +/− 7 nm | 678 +/− 7 nm | same |
| Radiant Energy (1) | 443 J | 443 J | same |
| Radiant Power (2) | 0.36 W | 0.36 W | same |
| Treatment Time | 20 minutes | 20 minutes | same |
| Radiant Exposure | 1.03 joules/cm$^2$ | 0.52 joules/cm$^2$ | half energy delivered each session. |
| Total Energy Delivered | 432 joules | 231 joules | half energy delivered each session. |
| Nominal Scalp Treatment Area | 420 cm$^2$ | 420 cm$^2$ | same |
| Treatment Schedule | 2 times per week | 4 times per week | double the number of sessions per week. |
| Power Source: | Li #18650, 2200 mA, 3.7 V, length 6.5 cm | Li #18500, 1600 mA, 3.7 V, length 5 cm | slightly smaller lithium battery |
| AC Charger | 5 VDC 1.5 amp | 5 VDC 1.5 amp | same charging capability |
| Plastic Formulation Dome | | | difference only in color |
| Controller Board | TD-CONTROLLER-I | TD-CONTROLLER-I | same |
| IFU | K122950 | to be done | reflects change in model number and dome graphic, functionality and features same. |
| Firmware Revision/ Specifications | Version 109 | Version 109 | |

FIGS. 10A-10D represents an alternative outer shell design for a photo-bio-stimulation helmet device 1000. One of the most prominent features seen here are the dozens of ventilation holes that promote cooling and prevent more than a two-degree F.° rise in temperature inside the helmet over the ambient temperature just outside the helmet during use.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A low-level laser-light scalp-hair therapy device, comprising:
   a plastic helmet having on its interior a plurality of laser diode arrays mounted such as to generally direct a number of monochromatic and coherent therapeutic lights across the scalp of a user wearing it;
   a rechargeable battery and an operational status display that are mounted together with a master-switch, and which are all disposed within the plastic helmet;
   a controller connected to operate the plurality of laser diode arrays according to predefined therapeutic profiles and sessions, and that maintains an operational status and log with a microcontroller;
   a proximity sensor positioned as a user scalp presence detector, and connected to the controller to shut off power from the rechargeable battery to the plurality of laser diode arrays if the user scalp is not then detected as being proximate;
   at least one temperature sensor connected to the controller and connected to shut off battery power to the plurality of laser diode arrays if a particular part or area of the therapy device exceeds a predefined temperature;
   a speech synthesizer and a loudspeaker connected to the controller to audibly speak instructions and the operational status of the device to the user in a spoken language; and
   a wireless transceiver for Internet communication with a centralized server, and connected to exchange status and operational data with the controller.

2. The scalp-hair therapy device of claim 1, wherein:
   the plastic helmet is further fenestrated with a number of cooling air vents to pass any air heated during operation from inside to outside and to provide for cooling; and
   the cooling air vents are configured such that temperature rises inside the helmet during operation are limited to two degrees Fahrenheit over ambient outside.

3. The scalp-hair therapy device of claim 1, wherein:
   the plurality of laser diode arrays are each assembled from a number of vertical cavity surface emitting laser (VCSEL) devices operating at a wavelength of about 678-nm and that are distributed over one side of a flexible printed circuit mounted by studded bosses inside the plastic helmet.

4. The scalp-hair therapy device of claim 3, further comprising:
   a plurality of petal cutouts in the outside edges of the flexible printed circuit that are symmetrical along a central spine, and that then permit the flexible printed circuit to be cupped into and attached inside a concave bottom side of the plastic helmet.

5. The scalp-hair therapy device of claim 4, further comprising:
   a color-variable and intensity-variable light mounted inside the master-switch and electrically connected to the controller and having digital logic that communicates the operational status of the scalp-hair therapy device by modulating the color and intensity of a light visible to a user.

6. The scalp-hair therapy device of claim 5, further comprising:
- a number of separate external panels that are attached to the outside of a domed outer shell of the plastic helmet, and that include studded bosses that pass through reliefs in the domed outer shell to provide the studded bosses to which the flexible printed circuit is attached.

7. A low-level, laser-light, scalp-hair therapy device having on its interior a plurality of power-controlled laser diode arrays mounted to generally direct a monochromatic and coherent therapeutic light across the scalp of a user wearing it, comprising:
- a plastic helmet fenestrated with cooling air vents to pass any air heated during operation from inside to outside for cooling;
- a rechargeable battery and an operational status display and that are mounted together with a master-switch within the plastic helmet;
- a controller connected to apply operational power to the plurality of power-controlled laser diode arrays according to predefined therapeutic profiles and sessions, and that maintains an operational status and log with a microcontroller;
- a proximity sensor positioned as a user scalp presence detector, and connected to signal the controller to shut off battery power to the plurality of power-controlled laser diode arrays if the user scalp is not then detected as being proximate;
- at least one temperature sensor connected to the controller and connected to shut off battery power to the plurality of power-controlled laser diode arrays if a particular part or area of the therapy device exceeds a predefined temperature;
- a speech synthesizer and a loudspeaker connected to the controller and that speak instructions and the operational status of the device to the user in a spoken language;
- a wireless transceiver capable of Internet communication with a centralized server, and connected to exchange status and operational data with the controller;
- a plurality of petal cutouts in the outside edges of a flexible printed circuit that are symmetrical along a central spine, and that then permit the flexible printed circuit to be cupped into and attached inside a concave bottom side of the plastic helmet;
- a color-variable and intensity-variable light mounted inside the master-switch and electrically connected to the controller and having digital logic that can communicates the operational status of the scalp-hair therapy device by modulated light made visible to a user;
- separate external panels that are attached from outside a domed outer shell of the plastic helmet, and that include studded bosses that pass through reliefs in the domed outer shell to provide the studded bosses to which the flexible printed circuit is attached; and
- wherein, the vents are such that temperature rises inside the helmet during operation are limited to two degrees Fahrenheit over ambient outside; and
- wherein, the laser arrays are assembled from a number of vertical cavity surface emitting laser (VCSEL) devices operating at a wavelength of about 678-nm and distributed over one side of the flexible printed circuit mounted by studded bosses inside the plastic helmet.

* * * * *